(12) United States Patent
Hirai et al.

(10) Patent No.: US 6,387,362 B1
(45) Date of Patent: May 14, 2002

(54) ADSORBENT FOR BRADYKININ, METHOD FOR ELIMINATING THE SAME BY ADSORPTION, AND ADSORBER

(75) Inventors: Fumiyasu Hirai, Amagasaki; Nobutaka Tani, Osaka; Takamune Yasuda; Takashi Asahi, both of Kobe, all of (JP)

(73) Assignees: Kanegafuchi Kagaku Kogyo; Kabushiki Kaisha, both of Osaka (JP)

( * ) Notice: Subject to any disclaimer, the term of this patent is extended or adjusted under 35 U.S.C. 154(b) by 0 days.

(21) Appl. No.: 09/043,537

(22) PCT Filed: Aug. 23, 1996

(86) PCT No.: PCT/JP96/02371

§ 371 Date: Aug. 14, 1998

§ 102(e) Date: Aug. 14, 1998

(87) PCT Pub. No.: WO97/10897

PCT Pub. Date: Mar. 27, 1997

(51) Int. Cl.[7] .................... A61K 31/795; B01D 15/04
(52) U.S. Cl. ............... 424/78.13; 210/646; 210/647; 210/692; 210/638; 502/402; 530/416
(58) Field of Search ................. 424/484, 501, 424/486, 78.18, 78.13; 210/646–47, 638, 679, 692; 502/402; 514/2, 15; 530/416, 417, 314

(56) References Cited

U.S. PATENT DOCUMENTS

| | | | |
|---|---|---|---|
| 3,876,775 A | | 4/1975 | Izaka et al. |
| 4,200,695 A | * | 4/1980 | Chong et al. |
| 4,221,778 A | * | 9/1980 | Raghunathan |
| 4,251,510 A | * | 2/1981 | Tankersley |
| 5,407,581 A | * | 4/1995 | Onodera et al. |

FOREIGN PATENT DOCUMENTS

| | | |
|---|---|---|
| JP | 56-152740 A | 11/1981 |
| JP | 58-154655 A | 9/1983 |
| JP | 6-296861 A | 10/1994 |
| JP | 6-296864 A | 10/1994 |

* cited by examiner

*Primary Examiner*—Edward J. Webman
(74) *Attorney, Agent, or Firm*—Fish & Neave

(57) ABSTRACT

An adsorbent or bradykinin comprising styrene-divinylbenzene copolymer having sulfonic acid groups and a method for adsorbing and removing bradykinin comprising contacting the adsorbent with a fluid containing bradykinin are provided. An adsorber for adsorbing bradykinin in which the adsorbent is charged in a vessel having an inlet and an outlet for a fluid is also provided.

9 Claims, 1 Drawing Sheet

ADSORBENT FOR BRADYKININ, METHOD FOR ELIMINATING THE SAME BY ADSORPTION, AND ADSORBER

TECHNICAL FIELD

The present invention relates to an adsorbent for bradykinin, a process for adsorbing and removing the same using the adsorbent, and an adsorber of the same.

BACKGROUND ART

Bradykinin is a physiologically active peptide consisting of nine amino acids, which was discovered by Rochae Silva in 1949. It is known that bradykinin has various activities, such as a hypotensive effect and an increase in vascular permeability via vasodilation, a contractive effect on smooth muscle, and the like.

The mechanism for production of bradykinin is considered to be as follows. First, blood coagulation factor XII is activated into blood coagulation factor XIIa by insoluble materials such as glass, kaolin or the like having negative charge on their solid phase surface, eladic acid, trypsin, plasmin or kallikrein. The blood coagulation factor XIIa then converts prekallikrein in blood into kallikrein. The kallikrein in turn reacts with high molecular weight kininogen in blood to release bradykinin. On the other hand, the kallikrein produced during this process has a property of activating blood coagulation factor XII (positive feedback). The released bradykinin is degraded by kininase II (which is the same enzyme as the angiotensin I converting enzyme).

Recently, hemocatharsis by means of an extracorporeal circulation has been extensively carried out. It has become a problem that, upon the hemocatharsis, bradykinin sometime happens to be produced due to a contact of some kind of medical materials with blood and/or plasma to cause a shock-like symptom. In the case of septicemia, it is consdered that bradykinin is produce due to an endotoxin to cause hypotension which induces shock.

The mechanism of the production of bradykinin due to some kind of medical materials is hypothesized as follows. Prekallikrein exists in blood which is bound to high molecular weight kininogen. Some kind of medical materials have a property of adsorbing both of the prekallikrein/high molecular weight kininogen complex and the blood coagulation factor XII. Thus, substances involved in the production system of bradykinin are gathered which promote the production of bradykinin.

Under these circumstances, development of an adsorbent for removing bradykinin from blood has been desired. As an adsorbent for removing bradykinin from blood, an adsorbent with a hydrophobic property is disclosed in Japanese Laid-Open Publication No. 6-296861 and No. 6-296864 in the name of ASAHI MEDICAL CO., LTD.. However, since, in general, hydrophobic materials adsorb critical proteins in blood as well, these materials are inappropriate as materials for hemocatharsis.

DISCLOSURE OF THE INVENTION

As a result of the extensive investigation on an appropriate carrier to remove the above-mentioned bradykinin, the inventors found that a styrene-divinylbenzene copolymer having sulf onic acid groups was effective for such a removal. Based on this finding, the inventors obtained the present invention.

The present invention provides an adsorbent for bradykinin comprising a styrene-divinylbenzene copolymer having sulfonic acid groups.

In one embodiment, an ion exchange capacity of the styrene-divinylbenzene copolymer having sulfonic acid groups is between about 0.01 meq/ml and about 5 meq/ml.

The present invention also provides a method for removing bradykinin, wherein the method comprises contacting an adsorbent comprising a styrene-divinylbenzene copolymer having sulfonic acid groups with a fluid containing bradykinin.

In one embodiment, an ion exchange capacity of the styrene-divinylbenzene copolymer having sulfonic acid groups is between about 0.01 meq/ml and about 5 meq/ml.

In one embodiment, the adsorbent is charged in a vessel having an inlet and an outlet for a fluid.

In one embodiment, the vessel is incorporated in an extracorporeal circulation circuit.

The present invention further provides an adsorber for adsorbing bradykinin, wherein the adsorber comprises a vessel which has an inlet and an outlet for a fluid and the vessel is charged with an adsorbent for bradykinin comprising a styrene-divinylbenzene copolymer having sulfonic acid groups.

In one embodiment, the adsorber is equipped with a means for preventing the adsorbent from flowing out of the vessel.

The present invention further provides a method for treating a disease of which the causal agent is bradykinin, wherein the method comprises contacting an adsorbent comprising a styrene-divinylbenzene copolymer having sulfonic acid groups with a body fluid from a patient with the disease.

In one embodiment, the adsorbent is charged in a vessel having an inlet and an outlet for a fluid.

In one embodiment, the vessel is incorporated in an extracorporeal circulation circuit.

In one embodiment, the disease is an inflammatory disease.

BEST MODE FOR CARRYING OUT THE INVENTION

Figure 1:
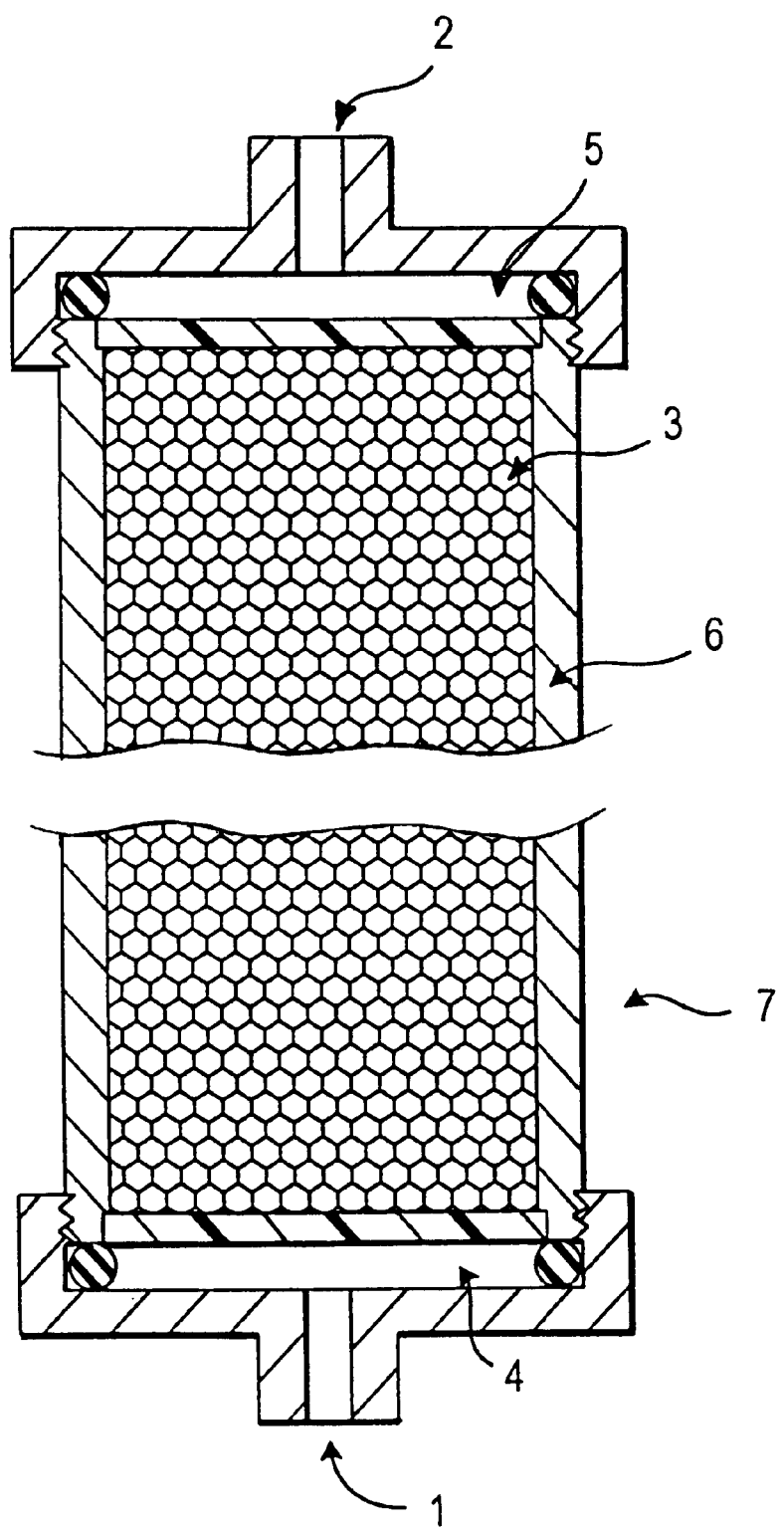
FIG. 1 is a schematic cross sectional view of one exemplary adsorber for bradykinin of the present invention. The symbols in the figure indicate, 1: an inlet or an outlet for a fluid; 2: an inlet or an outlet for a fluid; 3: an adsorbent for bradykinin; 4 and 5: a filter; 6: a column, and 7: a vessel.

As used herein, a fluid means a liquid containing bradykinin, which includes a body fluid. A body fluid includes blood, plasma, serum, ascites, lymph, synovia and a fractionated component therefrom, and other liquid components derived from an organism.

The styrene-divinylbenzene copolymer having sulfonic acid groups of the present invention is generally used as a strong acidic cation exchange resin. It can be in a form of, without limitation, particles, a board, a film, fibers and the like.

In case where the adsorbent is used while charged in a column and is used for body fluid, it is preferable that enough open spaces are made in the column such that cells in the body fluid can pass smoothly through them.

In a case where the adsorbent is in a particle form, it is preferably not fine particles, and it is preferable that the diameter of the particles is approximately 200 µm or more. More preferably, it may be used under a condition where particles which are either too small or too large are excluded, that is, under the condition that the distribution of the particle size is restricted and the average size of the particles is approximately 200 μm to approximately 1,000 μm. If the average size of the particles is less than approximately 200 μm, the flow of the fluid may become insufficient.

In case a where the adsorbent is in a form of hollow fibers, the adsorbent is preferably used for a body fluid. It is preferable that the inner diameter of the hollow fibers be approximately 5 μm or more. If the inner diameter is less than approximately 5 μm, cells in the body fluid may not pass smoothly. In a case where the adsorbent is in a form of fibers and is packed (not hollow), it is preferable that the diameter be approximately 1 μm or more. If the diameter is less than approximately 1 μm, cells in the body fluid may be adsorbed non-specifically.

In order to avoid non-specific adsorption of blood cell components while blood passes through the adsorbent, for example, the adsorbent may be coated with an appropriate macromolecule such as a polymer of hydroxyethyl-methacrylate. This coating can also prevent the adsorbent from generating fine particles.

There are various copolymerization methods to obtain the styrene-divinylbenzene copolymer of the present invention, and any of the methods can be used. Typically, a method can be used in which an appropriate amount of divinylbenzene is added to styrene, and a polymerization catalyst (for example, a small amount of benzoyl peroxide and water) is added along with a suspension agent such as bentonite or alginic acid, and the mixture is stirred vigorously to allow polymerization.

There are various kinds of methods for introducing sulfonic acid groups into styrene-divinylbenzene copolymer of the present invention. For example, thq method includes, but is not limited to, treating the above-mentioned copolymer with concentrated sulfuric acid or chlorosulfonic acid.

The amount of the sulfonic acid groups introduced to the styrene-divinylbenzene copolymer can be expressed as the ion exchange capacity. Sulfonic acid groups should be introduced into the copolymer in an appropriate density such that bradykinin is adsorbed. It is desirable that sulfonic acid groups are introduced into the copolymer in order to ensure that predominant proteins are not adsorbed non-specifically. The adsorbent ion exchange capacity of the present invention is preferably approximately 0.01 to approximately 5 meq/ml, more preferably approximately 0.1 to approximately 2 meq/ml. It is desirable that the ion exchange capacity is not less than approximately 0.01 meq/ml otherwise the ability of the adsorbent to adsorb bradykinin may be lowered. On the other hand, in a case where the ion exchange capacity is more than approximately 5 meq/ml, it is difficult to generate an adsorbent which maintains the ability to adsorb bradykinin.

The adsorbent of the present invention can adsorb bradykinin on its outer surface. It is desirable that the adsorbent has pores on its surface to increase its surface area, such that more bradykinin is adsorbed, wherein the size of the pores is enough for bradykinin to enter inside. The pore size varies and the distribution can be measured by means of a mercury porosimetry method or a nitrogen adsorption method. In order to adsorb bradykinin, the main distribution of the pore size is preferably approximately 25 to approximately 2,000 Å, more preferably approximately 100 to approximately 1,000 Å.

Although the adsorbent of the present invention can, as described above, adsorb bradykinin on its outer surface, it is desirable that the area of the surface per one adsorbent for adsorption (specific surface area), is increased for adsorbing more bradykinin. The specific surface area is preferably approximately 10 $m^2/g$ or more, more preferably approximately 100 $m^2/g$ or more.

There are various kinds of methods for adsorbing and removing bradykinin in a fluid comprising contacting the styrene-divinylbenzene copolymer having sulfonic, acid groups with the fluid. The typical methods are as follows: one method coimprising taking out the fluid, storing it in a bag or the like, mixing it with the adsorbent to remove bradykiin and removing the adsorbent by filtration to obtain a fluid free of bradyknin; and another method in which the fluid is passed through a vessel in which the adsorbent is charged, wherein the vessel has an inlet and an outlet for a fluid and is equipped with a filter at the outlet through which the fluid can pass preventing the adsorbent from flowing out, and the like. Although either of the methods can be used, the latter method is more suitable for the adsorbent of the present invention since it is easy to operate and is capable of effectively removing bradykinin from the fluid from patients using an in-line system in which the vessel is incorporated in an extracorporeal circulation circuit.

Next, the adsorber for bradykinin of the present invention is explained based on a schematic cross sectional view of FIG. 1. However, the adsorber of the present invention is not limited to this example.

The vessel 7 shown in the FIG. 1 has: an inlet 1 or an outlet for a fluid, an outlet 2 or an inlet for a fluid, the adsorbent 3 for bradykinin of the present invention, means 4 and 5 to prevent the adsorbent 3 from flowing out, through which the fluid and the component contained in the fluid can pass, and a column 6. The form and material of the vessel 7 are not specifically limited. However, for example, a cylindrical vessel having a capacity of approximately 150 to approximately 400 ml and a diameter of approximately 4 to approximately 10 cm is preferably used.

Hereinafter, the present invention will be specifically described by way of examples. However, the invention is not limited to the examples.

EXAMPLE

A strong acidic cation-exchange resin Diaion HPK-55H (MITSUBISHI KASEI CORPORATION, a styrene-divinylbenzene copolymer having sulfonic acid groups and having an ion exchange capacity of about 1 meq/ml) was converted into Na-type, and equilibrated with physiological saline. Then, 0.5 ml of this ion-exchange resin was placed into a test tube and excess physiological saline was removed. 3 ml of human serum containing about 120 ng/ml of bradykinin was added to the resin, and the mixture was shaken at 37° C. for 2 hours. The concentration of the bradykinin in the supernatant was determined by using a commercially available quantifying reagent (MARKIT ( A Bradykinin, DAINIPPON PHARMACEUTICAL CO. LTD.). No bradykinin was detected.

Comparative Example

In stead of the ion exchange resin, 0.5 ml of physiological saline was placed into a test tube, 3 ml of human serum containing about 120 ng/ml of bradykinin was added to the saline, and the mixture was shaken at 37° C. for 2 hours. The concentration of the bradykinin in the supernatant was determined, as described in Example, to be 103 ng/ml.

(Results)

It was found that the concentration of. bradykinin in the Example was greatly lowered as compared with that in the Comparative Example, and that bradykinin in the fluid could be efficiently adsorbed to be removed by using the above-mentioned strong acidic cation-exchange resin.

Industrial Applicability

The adsorbent of the present invention comprising the styrene-divinylbenzene copolymer having sulfonic acid groups may be used to efficiently adsorb and remove bradykinin in a fluid. The present invention may provide an effective method to suppress the action of bradykinin in various diseases of which the causal agent is bradykinin (for example, an inflammatory disease and the like).

What is claimed is:

1. A method for removing bradykinin from body fluids, wherein the method comprises contacting an adsorbent comprising a styrene-divinylbenzene copolymer having sulfonic acid groups with a body fluid containing bradykinin.

2. The method according to claim 1, wherein an ion exchange capacity of said styrene-divinylbenzene copolymer having sulfonic acid groups is between about 0.01 meq/ml and about 5 meq/ml.

3. The method according to claim 1, wherein said adsorbent is charged in a vessel having an inlet and an outlet for the fluid.

4. The method according to claim 3, wherein said vessel is incorporated in an extracorporeal circulation circuit.

5. A method for treating a disease of which the causal agent is bradykinin, wherein. the method comprises contacting an adsorbent for bradykinin comprising a styrene-divinylbenzene copolymer having sulfonic acid groups with a body fluid from a patient with the disease.

6. The method according to claim 5, wherein said adsorbent is charged in a vessel having an inlet and an outlet for the fluid.

7. The method according to claim 6, wherein said vessel is incorporated in an extracorporeal circulation circuit.

8. The method according to claim 5, wherein said disease is an inflammatory disease.

9. Use of an adsorbent for bradykinin in a method for treating a disease of which the causal agent is bradykinin wherein the adsorbent comprises a styren-divinylbenzene copolymer having sulfonic acid groups, and the method comprises charging the adsorbent in a vessel; incorporating the vessel in an extracorporeal circulation circuit in an in-line system; and removing bradykinin from a body fluid from a patient which is passed through the extracorporeal circulation circuit.

* * * * *